United States Patent [19]
Skotnicki et al.

[11] Patent Number: 5,362,718
[45] Date of Patent: Nov. 8, 1994

[54] RAPAMYCIN HYDROXYESTERS

[75] Inventors: Jerauld S. Skotnicki, Allentown; Christina L. Leone, Princeton, both of N.J.; Guy A. Schiehser, Yardley, Pa.

[73] Assignee: American Home Products Corporation, Madison, N.J.

[21] Appl. No.: 229,261

[22] Filed: Apr. 18, 1994

[51] Int. Cl.$^5$ ............... A61K 31/695; A61K 31/395; C07D 498/16; C07D 7/04
[52] U.S. Cl. ...................... 514/63; 514/291; 540/452; 540/456
[58] Field of Search ............. 540/456, 452; 514/291, 514/63

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,375,464 | 3/1983 | Sehgal et al. | 424/122 |
| 4,401,653 | 8/1983 | Eng | 424/124 |
| 4,650,803 | 3/1987 | Stella et al. | 540/456 |
| 4,885,171 | 12/1989 | Surendra et al. | 424/122 |
| 5,023,262 | 6/1991 | Caufield et al. | 540/456 |
| 5,023,263 | 6/1991 | Von Burg | 540/456 |
| 5,023,264 | 6/1991 | Caulfield et al. | 514/291 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 514/183 |
| 5,100,899 | 3/1992 | Calne | 514/291 |
| 5,102,876 | 4/1992 | Caufield | 514/18.3 |
| 5,118,677 | 6/1992 | Caufield | 514/183 |
| 5,118,678 | 6/1992 | Kao et al. | 514/183 |
| 5,120,842 | 6/1992 | Failli et al. | 540/452 |
| 5,130,307 | 7/1992 | Failli et al. | 514/291 |
| 5,138,051 | 8/1992 | Hughes et al. | 540/456 |
| 5,151,413 | 9/1992 | Caufield et al. | 540/456 |
| 5,169,851 | 12/1992 | Hughes et al. | 514/291 |
| 5,177,203 | 1/1993 | Failli et al. | 540/456 |
| 5,194,447 | 3/1993 | Kao | 540/456 |
| 5,221,670 | 6/1993 | Caufield | 514/183 |
| 5,233,036 | 8/1993 | Hughes | 540/456 |
| 5,260,300 | 11/1993 | Hu | 540/456 |
| 5,262,423 | 11/1993 | Kao | 514/291 |
| 5,286,730 | 2/1994 | Caufield et al. | 514/291 |
| 5,286,731 | 2/1994 | Caufield et al. | 514/291 |
| 5,302,584 | 4/1994 | Kao et al. | 514/291 |

FOREIGN PATENT DOCUMENTS

507555A1 7/1992 European Pat. Off. ............ 540/456

OTHER PUBLICATIONS

Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant, 11 (pt. 2):197 (1992).
Stepkowski, S. M., Transplantation Proc. 23:507 (1991).

*Primary Examiner*—Robert T. Bond
*Attorney, Agent, or Firm*—Arnold S. Milowsky

[57] ABSTRACT

A compound of the structure (Abstract continued on next page.)

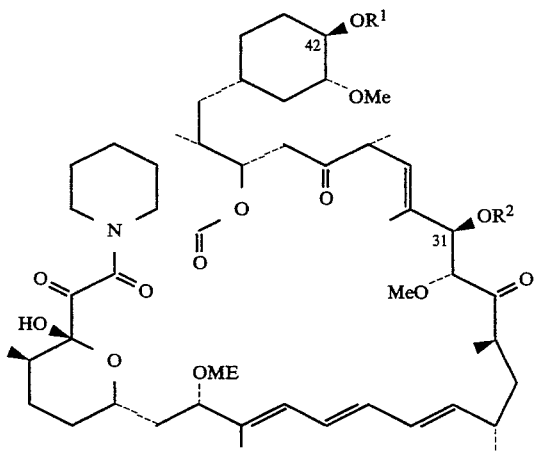

wherein $R^1$ and $R^2$ are each, independently, hydrogen or $-CO(CR^3R^4)_b(CR^5R^6)_dCR^7R^8R^9$;

$R^3$ and $R^4$ are each, independently, hydrogen, alkyl, alkenyl, alkynyl, trifluoromethyl, or $-F$;

$R^5$ and $R^6$ are each, independently, hydrogen, alkyl, alkenyl, alkynyl, $-(CR^3R^4)_fOR^{10}$, $-CF_3$, $-F$, or $-CO_2R^{11}$, or $R^5$ and $R^6$ may be taken together to form X or a cycloalkyl ring that is optionally mono-, di-, or tri-substituted with $-(CR^3R^4)_fOR^{10}$;

$R^7$ is hydrogen, alkyl, alkenyl, alkynyl, $-(CR^3R^4)_fOR^{10}$, $-CF_3$, $-F$, or $-CO_2R^{11}$;

$R^8$ and $R^9$ are each, independently, hydrogen, alkyl, alkenyl, alkynyl, $-(CR^3R^4)_fOR^{10}$, $-CF_3$, $-F$, or $-CO_2R^{11}$, or $R^8$ and $R^9$ may be taken together to form X or a cycloalkyl ring that is optionally mono-, di-, or tri-substituted with $-(CR^3R^4)_fOR^{10}$;

$R^{10}$ is hydrogen, alkyl, alkenyl, alkynyl, tri-(alkyl)silyl, tri-(alkyl)silylethyl, triphenylmethyl, benzyl, alkoxymethyl, tri-(alkyl)silylethoxymethyl, chloroethyl, or tetrahydropyranyl;

$R^{11}$ is hydrogen, alkyl, alkenyl, alkynyl, or phenylalkyl;

X is 5-(2,2-dialkyl)[1,3]dioxanyl, 5-(2,2-dicycloalkyl)[1,3]dioxanyl, 4-(2,2-dialkyl)[1,3]dioxanyl, 4-(2,2-dicycloalkyl)[1,3]dioxanyl, 4-(2,2dialkyl)[1,3-]dioxalanyl, or 4-(2,2-dicycloalkyl)[1,3]dioxalanyl;

$b = 0-6$;

$d = 0-6$; and $f = 0-6$ with the proviso that $R^1$ and $R^2$ are both not hydrogen and further provided that either $R^1$ or $R^2$ contains at least one $-(CR^3R^4)_fOR^{10}$, X, or $-(CR^3R^4)_fOR^{10}$ substituted cycloalkyl group, or a pharmaceutically acceptable salt thereof which is useful as an immunosuppressive, antiinflammatory, antifungal, antiproliferative, and antitumor agent.

24 Claims, No Drawings

RAPAMYCIN HYDROXYESTERS

BACKGROUND OF THE INVENTION

This invention relates to hydroxyesters of rapamycin and a method for using them for inducing immunosuppression, and in the treatment of transplantation rejection, graft vs. host disease, autoimmune diseases, diseases of inflammation, adult T-cell leukemia/lymphoma, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in *vitro* and *in vivo* [C. Vezina et al., J. Antibiot. 28, 721 (1975); S. N. Sehgal et al., J. Antibiot. 28, 727 (1975); H. A. Baker et al., J. Antibiot. 31,539 (1978); U.S. Pat. Nos. 3,929,992; and 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], smooth muscle cell proliferation and intimal thickening following vascular injury [Morris, R. J. Heart Lung Transplant 11 (pt. 2): 197 (1992)], adult T-cell leukemia/lymphoma [European Patent Application 525,960 A1], and ocular inflammation [European Patent Application 532,862 A1].

Mono- and diacylated derivatives of rapamycin (esterified at the 28 and 43 positions) have been shown to be useful as antifungal agents (U.S. Pat. No. 4,316,885) and used to make water soluble aminoacyl prodrugs of rapamycin (U.S. Pat. No. 4,650,803). Recently, the numbering convention for rapamycin has been changed; therefore according to Chemical Abstracts nomenclature, the esters described above would be at the 31- and 42- positions.

DESCRIPTION OF THE INVENTION

This invention provides derivatives of rapamycin which are useful as immunosuppressive, antiinflammatory, antifungal, antiproliferative, and antitumor agents having the structure

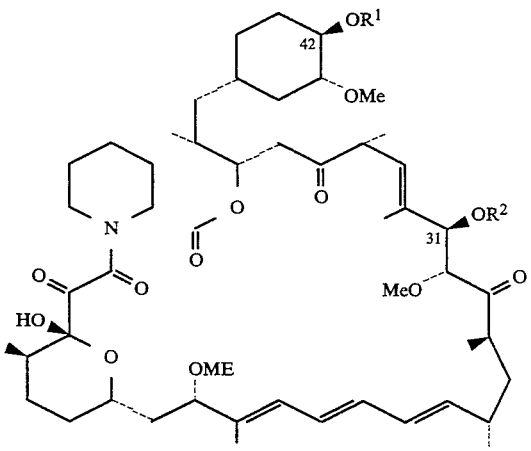

wherein $R^1$ and $R^2$ are each, independently, hydrogen or —$CO(CR^3R^4)_b(CR^5R^6)_dCR^7R^8R^9$;

$R^3$ and $R^4$ are each, independently, hydrogen, alkyl of 1–6 carbon atoms, alkenyl of 2–7 carbon atoms, alkynyl of 2–7 carbon atoms, trifluoromethyl, or —F;

$R^5$ and $R^6$ are each, independently, hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$, or $R^5$ and $R^6$ may be taken together to form X or a cycloalkyl ring of 3–8 carbon atoms that is optionally mono-, di-, or tri-substituted with —$(CR^3R^4)_fOR^{10}$;

$R^7$ is hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;

$R^8$ and $R^9$ are each, independently, hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$, or $R^8$ and $R^9$ may be taken together to form X or a cycloalkyl ring of 3–8 carbon atoms that is optionally mono-, di-, or tri-substituted with —$(CR^3R^4)_fOR^{10}$;

$R^{10}$ is hydrogen, alkyl of 1–6 carbon atoms, alkenyl of 2–7 carbon atoms, alkynyl of 2–7 carbon atoms, tri-(alkyl of 1–6 carbon atoms)silyl, tri-(alkyl of 1–6 carbon atoms)silylethyl, triphenylmethyl, benzyl, alkoxymethyl of 2–7 carbon atoms, tri-(alkyl of 1–6 carbon atoms)silylethoxymethyl, chloroethyl, or tetrahydropyranyl;

$R^{11}$ is hydrogen, alkyl of 1–6 carbon atoms, alkenyl of 2–7 carbon atoms, alkynyl of 2–7 carbon atoms, or phenylalkyl of 7–10 carbon atoms;

X is 5-(2,2-di-(alkyl of 1–6 carbon atoms))[1,3]dioxanyl, 5-(2,2-di-(cycloalkyl of 3–8 carbon atoms))[1,3]dioxanyl, 4-(2,2-di-(alkyl of 1–6 carbon atoms))[1,3]dioxanyl, 4-(2,2-di-(cycloalkyl of 3–8 carbon atoms))[1,3]dioxanyl, 4-(2,2-di-(alkyl of 1–6 carbon atoms))[1,3]dioxalanyl, or 4-(2,2-di-(cycloalkyl of 3–8 carbon atoms))[1,3]dioxalanyl;

b = 0–6;
d = 0–6; and
f = 0–6 with the proviso that $R^1$ and $R^2$ are both not hydrogen and further provided that either $R^1$ or $R^2$ contains at least one —$(CR^3R^4)_fOR^{10}$, X, or—$(CR^3R^4)_fOR^{10}$ substituted cycloalkyl of 3–8 carbon atoms group, or a pharmaceutically acceptable salt thereof.

The pharmaceutically acceptable salts are those derived from such inorganic cations such as sodium, potassium, and the like; and organic bases such as: mono-, di-, and trialkyl amines of 1-6 carbon atoms, per alkyl group and mono-. di-, and trihydroxyalkyl amines of 1-6 carbon atoms per alkyl group, and the like.

The terms alkyl of 1-6 carbon atoms, alkenyl of 2-7 carbon atoms, and alkynyl of 2-7 carbon atoms, include both straight chain as well as branched carbon chains. As the compounds of this invention can contain more than one —$(CR^3R^4)_fOR^{10}$ group, $R^3$, $R^4$, f, and $R^{10}$ can be the same or different. Similarly, when other generic substituent descriptions are repeated in the same structure, they can be the same or different.

For a compound in which $R^1$ contains $R^8$ and $R^9$ taken together to form X, where X is 5-(2,2-di-(alkyl of 1-6 carbon atoms))[1,3]dioxanyl, the alkyl group of X contains 1 carbon atom, and d=0, $R^1$ would have the following structure.

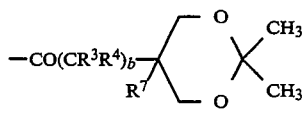

Similarly, for a compound in which $R^1$ contains $R^8$ and $R^9$ taken together to form X, where X is 4-(2,2-di-(cycloalkyl of 3-8 carbon atoms))[1,3]dioxanyl, the cycloalkyl group of X contains 6 carbon atom, and d=0, $R^1$ would have the following structure.

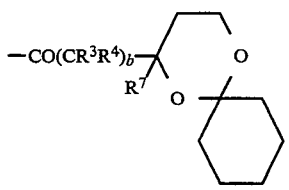

For compounds containing X, preferred compounds include those in which the alkyl group of X, if present, is methyl and the cycloalkyl group of X, if present, is cyclohexyl.

When $R^{10}$ is not hydrogen, alkyl, alkenyl, or alkynyl, it is intended that $R^{10}$ is a group that can serve as an alcohol protecting group. Thus, these groups are intermediates of free hydroxylated compounds, as well as being biologically active in their own right. $R^{10}$ covers tri-(alkyl of 1-6 carbon atoms)silyl, tri-(alkyl of 1-6 carbon atoms)silylethyl, triphenylmethyl, benzyl, alkoxymethyl of 2-7 carbon atoms, tri-(alkyl of 1-6 carbon atoms)silylethoxymethyl, chloroethyl, and tetrahydropyranyl groups. Other alcohol protecting groups are known by one skilled in the an and are also considered pan of this invention.

Of the compounds of this invention preferred members are those in which $R^2$ is hydrogen; those in which $R^2$ is hydrogen, b=0, and d=0; those in which $R^2$ is hydrogen, b=0, d=0, and $R^8$ and $R^9$ are each, independently hydrogen, alkyl, or —$(CR^3R^4)_fOR^{10}$, or are taken together to form X.

Compounds of this invention having the ester group —$CO(CR^3R^4)_bCR^5R^6)_d(CR^7R^8R^9)_e$ at the 42- or 31,42- positions can be prepared by acylation of rapamycin using protected hydroxy and polyhydroxy acids, alkoxy or polyalkoxy carboxylic acids that have been activated, followed by removal of the alcohol protecting groups, if so desired. Several procedures for carboxylate activation are known in the art, but the preferred methods utilize carbodiimides, mixed anhydrides, or acid chlorides. For example, an appropriately substituted carboxylic acid can be activated as a mixed anhydride, with an acylating group such as 2,4,6-trichlorobenzoyl chloride. Treatment of rapamycin with the mixed anhydride under mildly basic condition provides the desired compounds. Alternatively, the acylation reaction can be accomplished with 1-(3-dimethylaminopropyl)-3-ethylcarbodiimide hydrochloride and dimethylaminopyridine. Mixtures of 42- and 31,42-esters can be separated by chromatography.

The 31-ester-42-hydroxy compounds of this invention can be prepared by protecting the 42-alcohol of rapamycin with a protecting group, such as with a tert-butyl dimethylsilyl group, followed by esterification of the 31-position by the procedures described above. The preparation of rapamycin 42-silyl ethers is described in U.S. Pat. No. B1 5,120,842, which is hereby incorporated by reference. Removal of the protecting group provides the 31-esterified compounds. In the case of the tert-butyl dimethylsilyl protecting group, deprotection can be accomplished under mildly acidic conditions, such as acetic acid/water/THF. The deprotection procedure is described in Example 15 of U.S. Pat. No. 5,118,678, which is hereby incorporated by reference.

Having the 31-position esterified and the 42-position deprotected, the 42-position can be esterified using a different acylating agent than was reacted with the 31-alcohol, to give compounds having different esters at the 31- and 42- positions. Alternatively, the 42-esterified compounds, prepared as described above, can be reacted with a different acylating agent to provide compounds having different esters at the 31-and 42-positions.

This invention also covers analogous hydroxy esters of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; and 15-hydroxyrapamycin [U.S. Pat. No. 5,102,876]. The disclosures in the above cited U.S. Patents are hereby incorporated by reference.

Immunosuppressive activity for representative compounds of this invention was evaluated in an in vitro standard pharmacological test procedure to measure the inhibition of lymphocyte proliferation (LAF) and in two in vivo standard pharmacological test procedures. The pinch skin graft test procedure measures the immunosuppressive activity of the compound tested as well as the ability of the compound tested to inhibit or treat transplant rejection. The adjuvant arthritis standard pharmacological test procedure, which measures the ability of the compound tested to inhibit immune mediated inflammation. The adjuvant arthritis test procedure is a standard pharmacological test procedure for rheumatoid arthritis. The procedures for these standard pharmacological test procedures are provided below.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from nondrug treated controls. For each compound evaluated, rapamycin was also evaluated for the purpose of comparison. An IC$_{50}$ was obtained for each test compound as well as for rapamycin. When evaluated as a comparator for the representative compounds of this invention, rapamycin had an IC$_{50}$ ranging from 0.6–1.5 nM. The results obtained are provided as an IC$_{50}$ and as the percent inhibition of T-cell proliferation at 0.1 μM. The results obtained for the representative compounds of this invention were also expressed as a ratio compared with rapamycin. A positive ratio indicates immunosuppressive activity. A ratio of greater than 1 indicates that the test compound inhibited thymocyte proliferation to a greater extent than rapamycin. Calculation of the ratio is shown below.

$$\frac{IC_{50} \text{ of Rapamycin}}{IC_{50} \text{ of Test Compound}}$$

Representative compounds of this invention were also evaluated in an in vivo test procedure designed to determine the survival time of pinch skin graft from male BALB/c donors transplanted to male C$_3$H(H-2K) recipients. The method is adapted from Billingham R. E. and Medawar P. B., J. Exp. Biol. 28:385–402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days±S.D.) of the drug treatment group was compared with the control group. The following table shows the results that were obtained. Results are expressed as the mean survival time in days. Untreated (control) pinch skin grafts are usually rejected within 6–7 days. Compounds were tested using a dose of 4 mg/kg.

The adjuvant arthritis standard pharmacological test procedure measures the ability of test compounds to prevent immune mediated inflammation and inhibit or treat rheumatoid arthritis. The following briefly describes the test procedure used. A group of rats (male inbread Wistar Lewis rats) are pre-treated with the compound to be tested (1 h prior to antigen) and then injected with Freud's Complete Adjuvant (FCA) in the right hind paw to induce arthritis. The rats are then orally dosed on a Monday, Wednesday, Friday schedule from day 0–14 for a total of 7 doses. Both hind paws are measured on days 16, 23, and 30. The difference in paw volume (mL) from day 16 to day 0 is determined and a percent change from control is obtained. The left hind paw (uninjected paw) inflammation is caused by T-cell mediated inflammation and is recorded in the above table (% change from control). The right hind paw inflammation, on the other hand, is caused by non-specific inflammation. Compounds were tested at a dose of 5 mg/kg. The results are expressed as the percent change in the uninjected paw at day 16 versus control; the more negative the percent change, the more potent the compound. Rapamycin provided between −70% and −90% change versus control, indicating that rapamycin treated rats had between 70–90% less immune induced inflammation than control rats.

The results obtained in these standard pharmacological test procedures are provided following the procedure for making the specific compounds that were tested.

The results of these standard pharmacological test procedures demonstrate immunosuppressive activity both in vitro and in vivo for the compounds of this invention. The results obtained in the LAF test procedure indicates suppression of T-cell proliferation, thereby demonstrating the immunosuppressive activity of the compounds of this invention. Further demonstration of the utility of the compounds of this invention as immunosuppressive agents was shown by the results obtained in the skin graft and adjuvant arthritis standard pharmacological test procedures. Additionally, the results obtained in the skin graft test procedure further demonstrates the ability of the compounds of this invention to treat or inhibit transplantation rejection. The results obtained in the adjuvant arthritis standard pharmacological test procedure further demonstrate the ability of the compounds of this invention to treat or inhibit rheumatoid arthritis.

Based on the results of these standard pharmacological test procedures, the compounds are useful in the treatment or inhibition of transplantation rejection such as kidney, heart, liver, lung, bone marrow, pancreas (islet cells), cornea, small bowel, and skin allografts, and heart valve xenografts; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like), and eye uveitis.

Because of the activity profile obtained, the compounds of this invention also are considered to have antitumor, antifungal activities, and antiproliferative activities. The compounds of this invention therefore also useful in treating solid tumors, adult T-cell leukemia/lymphoma, fungal infections, and hyperproliferative vascular diseases such as restenosis and atherosclerosis. When used for restenosis, it is preferred that the compounds of this invention are used to treat restenosis that occurs following an angioplasty procedure. When used for this purpose, the compounds of this invention can be administered prior to the procedure, during the procedure, subsequent to the procedure, or any combination of the above.

When administered for the treatment or inhibition of the above disease states, the compounds of this invention can be administered to a mammal orally, parenterally, intranasally, intrabronchially, transdermally, topically, intravaginally, or rectally.

It is contemplated that when the compounds of this invention are used as an immunosuppressive or antiinflammatory agent, they can be administered in conjunction with one or more other immunoregulatory agents.

Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The compounds of this invention can be formulated neat or with a pharmaceutical carrier to a mammal in need thereof. The pharmaceutical carrier may be solid or liquid. When formulated orally, it has been found that 0.01% Tween 80 in PHOSAL PG-50 (phospholipid concentrate with 1,2-propylene glycol, A. Nattermann & Cie. GmbH) provides an acceptable oral formulation.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1-5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 $\mu$g/kg-100 mg/kg, preferably between 0.001-25 mg/kg, and more preferably between 0.01-5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example., packeted powders, vials, ampoules, prefilled syringes or sachets containing liquids. The unit dosage form can be, for example, a capsule or tablet itself, or it can be the appropriate number of any such compositions in package form.

The following examples illustrate the preparation and biological activities of representative compounds of this invention.

EXAMPLE 1

Rapamycin 42-ester with (tetrahydropyran-2-yloxy)acetic acid 2,4,6-Trichlorobenzoyl chloride (0.55 mL, 3.51 mmol) was added via syringe to a solution of the glycolic acid THP-ether (0.562 g, 3.51 mmol) and triethylamine (0.49 mL, 3.51 mmol) in 10 mL THF at 0 ° C. under nitrogen. The mixture was stirred for 4 h at room temperature, and a white precipitate formed. The white precipitate was removed by vacuum filtration and the filtrate was concentrated with a stream of nitrogen and warm water bath. The residue was dissolved in 10 mL benzene, then rapamycin (2.92 g, 3.19 mmol) and DMAP (0.429 g, 3.51 mmol) were added and the mixture was stirred overnight at room temperature. The mixture was diluted with EtOAc, washed with cold 1N HCl (aq), saturated NaHCO$_3$ (aq) and brine, dried over MgSO$_4$, filtered and concentrated to an oily yellow solid. Flash chromatography (2X with 65% EtOAc-hexane) afforded the title compound (1.114 g, 33%) as a white solid.

(−)FAB-MS m/z 1055.5 (M$^-$), 590.3 (southern fragment), 463.2 (northern fragment). $^1$H NMR (400 MHz, d-6 DMSO) δ 4.60 (m, 1 H, C(42)H), 4.66 (m, 1H), 4.14 (s, 2H), 3.73 (m, 1H), 3.42 (m, 1H). $^{13}$C NMR (100.6 MHz, d-6 DMSO) δ 169.2, 97.4, 63.5, 61.2, 29.7, 24.8. 18.8.

EXAMPLE 2

Rapamycin 42-ester with hydroxyacetic acid p-Toluenesulfonic acid (10 mg) was added to a solution of the product of Example 1 (306 mg, 0.29 mmol) in 10 mL CH$_3$OH at 0 ° C. The solution was stirred 2 h at room temperature, then quenched with saturated NaHCO$_3$ solution. The aqueous phase was extracted 3X with EtOAc and the combined organic phases were washed with brine, dried over MgSO$_4$, filtered and concentrated to a white solid. Purification by flash chromatography (2X with EtOAc) afforded the title compound (145 mg, 51%) as a white solid.

(−) FAB-MS m/z 971.3 (M$^-$), 590 (southern fragment), 379.1 (northern fragment). $^1$H NMR (400 MHz, d-6 DMSO) δ 4.60 (m, 1H, C(42)H), 3.98 (s, 2H). $^{13}$C NMR (100.6 MHz, d-6 DMSO) δ 172.1, 59.7.

Results obtained in standard pharmacological test procedures:
LAF IC$_{50}$: 1.80 nM
LAF ratio: 0.83
Percent change in adjuvant arthritis versus control: −88%

EXAMPLE 3

Rapamycin 42-ester with 2,2-dimethyl-3-(tetrahydropyran-2-yloxy)propionic acid To a solution of the 2,2-dimethyl-3-hydroxypropionic acid THP-ether (0.319 g, 1.58 mmol) and triethylamine (0.22 mL, 1.58 mmol) in 5 mL dry THF at 0 ° C. under nitrogen was added 2,4,6-trichlorobenzoyl chloride (0.25 mL, 1.58 mmol) dropwise via syringe. The mixture was stirred 4.5 h at room temperature. The white precipitate was removed by vacuum filtration and the filtrate was concentrated with a stream of nitrogen and a warm water bath. The residue was dissolved in 5 mL benzene, then rapamycin (1.31 g, 1.43 mmol) and DMAP (0.193 g, 1.58 mmol) were added. The mixture was stirred overnight at room temperature, diluted with EtOAc, washed with 1N HCl (aq), saturated NaHCO$_3$ (aq), H$_2$O and brine, dried over MgSO$_4$, filtered and concentrated to a yellow oily solid. Flash chromatography (1X with 60% EtOAc-hexane, 1X with 55% EtOAc-hexane) afforded the title compound (0.356 g, 23%), as a white solid.

(−)FAB-MS m/z 1097.7 (M$^-$), 505.3 (northern fragment). $^1$H NMR (400 MHz, d-6 DMSO) δ 4.55 (m, 1H, C(42)H), 4.55 (m, 1H), 3.69 (m, 1H), 3.60 (m, 2H), 3.42 (m, 1H), 1.13 (s, 3H), 1.11 (s, 3H). $^{13}$C NMR (100.6 MHz, d-6 DMSO) δ 175.0, 98.0, 73.8, 60.7, 42.6, 30.0, 24.9, 22.0, 21.6, 18.7.

Results obtained in standard pharmacological test procedures:
LAF IC$_{50}$: 7.10 nM
LAF ratio: 0.34

EXAMPLE 4

Rapamycin 42-ester with 3-hydroxy-2,2-dimethylpropionic acid p-Toluenesulfonic acid (10 mg) was added to a solution of the product of Example 3 (250 mg, 0.23 mmol) in 10 mL CH$_3$OH at 0 ° C. The solution was stirred 2 hours at room temperature, then quenched with saturated NaHCO$_3$ solution. The aqueous phase was extracted 3X with EtOAc and the combined organic phases were washed with brine, dried over MgSO$_4$, filtered and concentrated to a white solid. Purification by flash chromatography (2X with 75% EtOAc-hexane) afforded the title compound (103 mg, 45%) as a white solid.

(−) FAB-MS m/z 1013.3 (M$^{31}$), 590.2 (southern fragment), 421.1 (northern fragment). $^1$H NMR (400 MHz, d-6 DMSO) δ 4.48 (m, 1H, C(42)H), 3.39 (d, 2H), 106 (s, 6H). $^{13}$C NMR (100.6 MHz, d-6 DMSO) δ 175.5, 68.0, 44.1, 21.7.

Results obtained in standard pharmacological test procedures:
LAF IC$_{50}$:0.80 nM
LAF ratio: 1.25
Skin graft survival time: 10.7±0.5 days

EXAMPLES 5 AND 6

Rapamycin 42-ester with 2,2-dimethyl[1,3]dioxalane-4-carboxylic acid (Ex. 5)
Rapamycin 31,42-diester with 2,2-dimethyl[1.3]dioxalane-4-carboxylic acid (EX. 6)

2,4,6-Trichlorobenzoyl chloride (0.56 mL, 3.61 mmol) was added via syringe to a solution of the 2,3-dihydroxypropionic acid isopropylidene ketal (0.527 g, 3.61 mmol) and triethylamine (0.50 mL, 3.61 mmol) in 10 mL THF at 0 ° C. under nitrogen. The mixture was stirred 4 h at room temperature. The white precipitate was removed by vacuum filtration and the filtrate was concentrated with a stream of nitrogen and warm water bath. The residue was dissolved in 15 mL benzene and rapamycin (3.00 g, 3.28 mmol), then DMAP (0.441 g, 3.61 mmol) were added and the mixture was stirred overnight at room temperature. The mixture was diluted with EtOAc, washed with cold 1N HCl (aq), saturated NaHCO$_3$ (aq) and brine, dried over MgSO$_4$, filtered and concentrated to a yellow foam. Flash chromatography on silica gel (gradient elution: 50–60-75-100% EtOAc-hexane, 4X with 65% EtOAc-hexane) afforded the title compounds. The less polar 31,42-diester (0.415 g) eluted first and the more polar 42-monoester (0.601 g, 16%) eluted second, and were isolated as white solids.

EXAMPLE 5

(−)FAB-MS m/z 1041.4 (M$^-$), 590.3 (southern fragment), 449.2 (northern fragment). $^1$H NMR (400 MHz, d-6 DMSO) δ 4.6 (m, 1H, C(42)H), 4.6 (m, 1H), 4.20 (dd, 1H), 3.96 (m, 1H), 1.36 (s, 3H), 1.30 (s, 3H). $^{13}$C NMR (100.6 MHz, d-6 DMSO) δ 170.5, 110.2, 73.4, 66.6, 25.7, 25.4.

EXAMPLE 6

(−)FAB-MS m/z 1169.6 (M−). $^1$H NMR (400 MHz, d-6 DMSO) δ 5.3 (m, 1H, C(31)H), 4.6 (m, 1H, C(42)H), 4.6 (m, 2H), 4.19 (t, 1H), 4.13 (t, 1H), 3.9 (m, 2H), 1.36 (s, 3H), 1.33 (s, 3H), 1.30 (s, 3H), 1.28 (s, 3H). $^{13}$C NMR (100.6 MHz, d-6 DMSO) δ 170.5, 169.2, 110.3, 110.2, 73.4, 66.6, 66.5, 25.8, 25.7, 25.4, 25.1.

Results obtained in standard pharmacological test procedures:

EXAMPLE 5

LAF IC$_{50}$: 1.20 nM
LAF ratio: 0.74

EXAMPLE 6

LAF IC$_{50}$: 1.30 nM
LAF ratio: 0.5

EXAMPLE 7

Rapamycin 42-ester with 2,3-dihydroxypropionic acid

A solution of the product of Example 5 (351 mg, 0.34 mmol) in 10 mL THF and 10 mL 1N HCl was stirred at room temperature for 6 h. The mixture was diluted with EtOAc, washed with saturated NaHCO$_3$ solution and brine, dried over MgSO$_4$, filtered and concentrated to an oil. Flash chromatography (1X with EtOAc, 1X with 10% MeOH-CH$_2$Cl$_2$, 1X with 5% MeOH-EtOAc) afforded the title compound (78 mg, 23%) as a white solid.

(−)FAB-MS m/z 1001.2 (M−), 590.2 (southern fragment), 409.1 (northern fragment). $^1$H NMR (400 MHz, d-6 DMSO) δ 5 4.5 (m, 1H, C(42)H), 3.60 (m, 1H), 3.45 (m, 2H).

Results obtained in standard pharmacological test procedures:
LAF IC$_{50}$: 1.4 nM
LAF ratio: 0.40

EXAMPLE 8

Rapamycin 42-ester with 2.2-dimethyl[1.3dioxane-5-carboxylic acid 2,4,6-Trichlorobenzoyl chloride (0.98 mL, 6.27 mmol) was added via syringe to a solution of the 2-(hydroxymethyl)-3-hydroxypropionic acid isopropylidene ketal (1.000 g, 6.24 mmol) and triethylamine (0.90 mL, 6.46 mmol) in 20 mL THF at 0 ° C. under nitrogen. The mixture was stirred for 4 h at room temperature, and a white precipitate formed. The white precipitate was removed by vacuum filtration and the filtrate was concentrated with a stream of nitrogen and warm water bath. The residue was dissolved in 20 mL benzene, then rapamycin (5.70 g, 6.24 mmol) and DMAP (0.762 g, 6.24 mmol) were added and the mixture was stirred overnight at room temperature. The mixture was diluted with EtOAc, washed with H$_2$O and brine, dried over MgSO$_4$, filtered and concentrated to a yellow solid. Flash chromatography (75% EtOAc-hexane) afforded the title compound (4.17 g, 63%) as a white solid.

(−)FAB-MS m/z 1055.8 (M−), 590.5 (southern fragment), 463.4 (northern fragment). $^1$H NMR (400 MHz, d-6 DMSO) δ 4.55 (m, 1H, C(42)H), 3.95 (m, 4H), 1.30 (s, 6H). $^{13}$C NMR (100.6 MHz, d-6 DMSO) δ 170.1, 97.4, 59.5, 24.8, 22.5.

Results obtained in standard pharmacological test procedures:
LAF IC$_{50}$: 0.76 nM
LAF ratio: 0.45

EXAMPLE 9

Rapamycin 42-ester with 3-hydroxy-2-hydroxymethylpropionic acid

A solution of the product of Example 8 (3.30 g, 3.12 mmol) in 50 mL THF and 25 mL 1N HCl was stirred 2 h at room temperature. The solution was diluted with saturated NaHCO$_3$ solution and extracted with EtOAc (3X). The combined organic phases were washed with saturated NaCl (aq), dried over MgSO$_4$, filtered and concentrated to a yellow foam. Purification by flash chromatography (1X with EtOAc; 2X with 5% EtOH-EtOAc) afforded the title compound (1.68 g, 53 %) as a white solid.

(−)FAB-MS m/z 1015.5 (M−), 590.3 (southern fragment), 423.3 (northern fragment). $^1$H NMR (400 MHz, d-6 DMSO) δ 4.6 (br s, 2H), 4.55 (m, 1H, C(42)H), 3.55 (m, 4H), 2.57–2.53 (m, 1H). $^{13}$C NMR (100.6 MHz, d-6 DMSO) δ 172.2, 59.3, 51.5.

Results obtained in standard pharmacological test procedures:
LAF IC$_{50}$: 0.84 nM
LAF ratio: 0.57

EXAMPLE 10

Rapamycin 42-ester with 2,2,5-trimethyl[1.3dioxane-5-carboxylic acid

To a solution of the 2,2-bis(hydroxymethyl)propionic acid isopropylidene ketal (1.041 g, 5.98 mmol) (prepared according to the procedure of Bruice, J. Am. Chem. Soc. 89:3568 (1967)) and triethylamine (0.83 mL, 5.98 mmol) in 20 mL anhydrous THF at 0 ° C. under nitrogen was added 2,4,6-trichlorobenzoyl chloride (0.93 mL, 5.98 mmol) and the resultant white suspension was stirred 5 h at room temperature. The precipitate was removed by vacuum filtration, rinsing the flask and filter cake with an additional 10 mL dry THF. The filtrate was concentrated by rotary evaporation to a white solid. The residue was dissolved in 20 mL dry benzene, then rapamycin (5.47 g, 5.98 mmol) and DMAP (0.731 g, 5.98 retool) were added. After stirring overnight at room temperature, the mixture was diluted with EtOAc, washed with H$_2$O and saturated NaCl (aq), dried over MgSO$_4$, filtered and evaporated to a yellow oil. Flash chromatography (5X with 60% EtOAc-hexane) afforded the title compound (2.2 g, 34%) as a white solid.

(−)FAB-MS m/z 1069.5 (M−), 590.3 (southern fragment), 477.2 (northern fragment). $^1$H NMR (400 MHz, d-6 DMSO) δ 4.57 (m, 1H, C(42)H, 4.02 (d, 2H), 3.60 (d, 2H), 1.34 (s, 3H), 1.24 (s, 3H), 1.06 (s, 3H). $^{13}$C NMR (100.6 MHz, d-6 DMSO) δ 173.2, 99.0, 65.0, 22.2, 18.1.

Results obtained in standard pharmacological test procedures:
LAF IC$_{50}$: 4.90 nM
LAF ratio: 0.41
Skin graft survival time: 11.0±1.3 days

EXAMPLE 11

Rapamycin 42-ester with 2,2-bis-(hydroxymethyl)propionic acid

A solution of the product of Example 10 (2.8 g, 2.65 mmol) in 50 mL THF and 25 mL 1N HCl was stirred at room temperature for 4 h. The mixture was diluted with water and extracted three times with EtOAc. The combined organic phases were washed with saturated NaHCO$_3$ solution, saturated NaCl solution, dried over MgSO$_4$, filtered and evaporated to a yellow oily solid. Purification by flash chromatography (3X with EtOAc) afforded the title compound (1.6 g, 59%).

(−)FAB-MS m/z 1029.6 (M−), 590.4 (southern fragment), 437.3 (northern fragment). $^1$H NMR (400 MHz, d-6 DMSO) δ 4.5 (m, 1H, C(42)H), 3.45 (s, 4H), 1.04 (s, 3H). $^{13}$C NMR (100.6 MHz, d-6 DMSO) δ 174.2, 63.7, 63.6, 49.9, 16.8.

Results obtained in standard pharmacological test procedures:

LAF IC$_{50}$: 0.80 and 1.80 nM
LAF ratio: 1.00 and 0.44
Skin graft survival time: 11.4±1.5 and 12.0±1.1 days
Percent change in adjuvant arthritis versus control: −88%

EXAMPLE 12

Rapamycin 42-ester with 2,2-dimethyl-5-(2-trimethylsilanylethoxymethyl)[1,3]dioxane-5-carboxylic acid 2,4,6-Trichlorobenzoyl chloride (0.14 mL, 0.86 mmol) was added via syringe to a solution of the 2,2-bis(hydroxymethyl)-2-(2-trimethylsilylethoxy)propionic acid isopropylidene ketal (0.250 g, 0.86 mmol) and triethylamine (0.12 mL, 0.86 mmol) in 2 mL THF at 0° C. under nitrogen. The mixture was stirred for 4 h at room temperature, and a white precipitate formed. The white precipitate was removed by vacuum filtration and the filtrate was concentrated with a stream of nitrogen and warm water bath. The residue was dissolved in 2 mL benzene, then rapamycin (0.786 g, 0.86 mmol) and DMAP (0.105 g, 0.86 mmol) were added and the mixture was stirred overnight at room temperature. The mixture was diluted with EtOAc, washed with H$_2$O and brine, dried over MgSO$_4$, filtered and concentrated to a yellow solid. Flash chromatography (gradient elution: 40-60-80-100% EtOAc-hexane) afforded the title compound (0.559 g, 54%) as a white solid.

(−)FAB-MS m/z 1185.2 (M−), 590.1 (southern fragment), 593 (northern fragment). $^1$H NMR (400 MHz, d-6 DMSO) δ 4.55 (m, 1H, C(42)H), 3.73 (m, 4H), 3.57 (s, 2 H), 3.43 (t, 2H), 1.29 (s, 6H), 0.79 (t, 2H), −0.04 (s, 9H). $^{13}$C NMR (100.6 MHz, d-6 DMSO) δ 171.1, 97.7, 70.2, 68.1, 61.3, 46.0, 24.6, 22.1, 14.6, −1.3.

Results obtained in standard pharmacological test procedures:

LAF IC$_{50}$: 7.20 nM
LAF ratio: 0.05

EXAMPLES 13 and 14

Rapamycin 42-ester with 3-methyl-1,5-dioxa-spiro[5.5]undecane 3-carboxylic acid (Ex. 13)

Rapamycin 31,42-diester with 3-methyl-1.5-dioxa-spiro[5.5]undecane 3-carboxylic acid (Ex. 14)

2,4,6-Trichlorobenzoyl chloride (0.16 mL, 1.0 mmol) was added via syringe to a solution of the 2,3-dihydroxypropionic acid cyclohexylidene ketal (0.214 g, 1.0 mmol) and triethylamine (0.14 mL, 1.0 mmol) in 2.5 mL THF at 0° C. under nitrogen. The mixture was stirred 4 h at room temperature. The white precipitate was removed by vacuum filtration and the filtrate was concentrated with a stream of nitrogen and warm water bath. The residue was dissolved in 3 mL benzene and rapamycin (0.457 g, 0.5 mmol), then DMAP (0.061 g, 0.5 mmol) were added and the mixture was stirred overnight at room temperature. The mixture was diluted with EtOAc, washed with cold 1N HCl (aq), saturated NaHCO$_3$ (aq) and brine, dried over MgSO$_4$, filtered and concentrated to a yellow foam. Flash chromatography on silica gel (45–50% EtOAc-hexane) afforded the title compounds. The 31,42-diester (0.168 g, 26% ) eluted first and the more polar 42-monoester (0.301 g, 52%) eluted second, and the products were isolated as white solids.

EXAMPLE 13

(−)FAB-MS m/z 1109.5 (M−), 590.3 (southern fragment), 517.3 (northern fragment). $^1$H NMR (400 MHz, d-6 DMSO) δ 4.55 (m, 1H, C(42)H), 3.61 (t, 4H), 1.04 (s, 3H). $^{13}$C NMR (100.6 MHz, d-6 DMSO) δ 173.3, 97.2, 64.2.

EXAMPLE 14

(−)FAB-MS m/z 1305.6 (M−). $^1$H NMR (400 MHz, d-6 DMSO) δ 5.25 (m, 1H, C(31)H), 4.55 (m, 1H, C(42)H), 3.64–3.54 (m, 8H), 1.05 (s, 3H), 0.97 (s, 3H). $^{13}$C NMR (100.6 MHz, d-6 DMSO) δ 173.2, 172.1, 97.3, 97.2, 64.3, 64.2, 63.9.

Results obtained in standard pharmacological test procedures:

EXAMPLE 13

LAF IC$_{50}$: 0.6 nM
LAF ratio: 2.00

EXAMPLE 14

LAF: inhibited T-cell proliferation by 43% at 0.1 μM

What is claimed is:

1. A compound of the structure

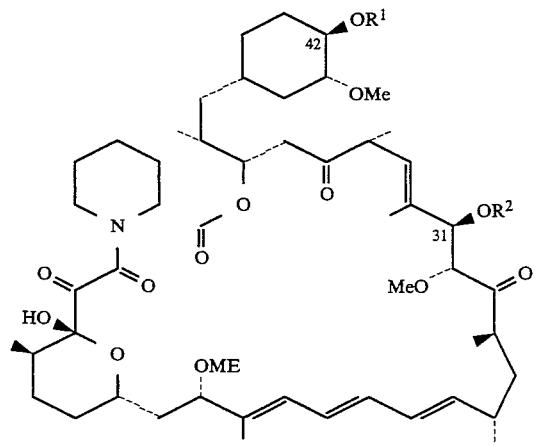

wherein R$^1$ and R$^2$ are each, independently, hydrogen or —CO(CR$^3$R$^4$)$_b$(CR$^5$R$^6$)$_d$CR$^7$R$^8$R$^9$;

R$^3$ and R$^4$ are each, independently, hydrogen, alkyl of 1–6 carbon atoms, alkenyl of 2–7 carbon atoms, alkynyl of 2-7 carbon atoms, trifluoromethyl, or —F;

$R^5$ and $R^6$ are each, independently, hydrogen, alkyl of 1-6 carbon atoms, alkenyl of 2-7 carbon atoms, alkynyl of 2-7 carbon atoms, —$(CR^3R^4)_fOR^{10}$, —$CF_3$, —F, or —$CO_2R^{11}$, or $R^5$ and $R^6$ may be taken together to form X or a cycloalkyl ring of 3-8 carbon atoms that is optionally mono-, di-, or tri-substituted with —$(CR^3R^4)_fOR^{10}$;

$R^7$ is hydrogen, alkyl of 1-6 carbon atoms, alkenyl of 2-7 carbon atoms, alkynyl of 2-7 carbon atoms, —$(CR^3R^4)_fOR^{10}$, —$CF_3$—F, or—$CO_2R^{11}$;

$R^8$ and $R^9$ are each, independently, hydrogen, alkyl of 1-6 carbon atoms, alkenyl of 2-7 carbon atoms, alkynyl of 2-7 carbon atoms, —$(CR^3R^4)_fOR^{10}$, —$CF_3$, —F, or —$CO_2R^{11}$, or $R^8$ and $R^9$ may be taken together to form X or a cycloalkyl ring of 3-8 carbon atoms that is optionally mono-, di-, or tri-substituted with —$(CR^3R^4)_fOR^{10}$;

$R^{10}$ is hydrogen, alkyl of 1-6 carbon atoms, alkenyl of 2-7 carbon atoms alkynyl of 2-7 carbon atoms, tri-(alkyl of 1-6 carbon atoms)silyl, tri-(alkyl of 1-6 carbon atoms)silylethyl, triphenylmethyl, benzyl, alkoxymethyl of 2-7 carbon atoms, tri-(alkyl of 1-6 carbon atoms)silylethoxymethyl, chloroethyl, or tetrahydropyranyl;

$R^{11}$ is hydrogen, alkyl of 1-6 carbon atoms, alkenyl of 2-7 carbon atoms, alkynyl of 2-7 carbon atoms, or phenylalkyl of 7-10 carbon atoms;

X is 5-(2,2-di-(alkyl of 1-6 carbon atoms))[1,3]dioxanyl, 5-(2,2-di-(cycloalkyl of 3-8 carbon atoms))[1,3]dioxanyl, 4-(2,2-di-(alkyl of 1-6 carbon atoms))[1,3]dioxanyl, 4-(2,2-di-(cycloalkyl of 3-8 carbon atoms))[1,3]dioxanyl, 4-(2,2-di-(alkyl of 1-6 carbon atoms))[1,3]dioxalanyl, or 4-(2,2-di-(cycloalkyl of 3-8 carbon atoms))[1,3]dioxalanyl;

b=0-6;
d=0-6 ; and
f=0-6 with the proviso that $R^1$ and $R^2$ are both not hydrogen and further provided that either $R^1$ or $R^2$ contains at least one —$(CR^3R^4)_fOR^{10}$, X, or —$(CR^3R^4)_fOR^{10}$ substituted cycloalkyl of 3-8 carbon atoms group, or a pharmaceutically acceptable salt thereof.

2. The compound of claim 1, wherein $R^2$ is hydrogen or a pharmaceutically acceptable salt thereof.

3. The compound of claim 2, wherein b=0 and d=0 or a pharmaceutically acceptable salt thereof.

4. The compound of claim 3, wherein $R^8$ and $R^9$ are each, independently hydrogen, alkyl, or —$(CR^3R^4)_fOR^{10}$, or are taken together to form X or a pharmaceutically acceptable salt thereof.

5. The compound of claim 1 which is rapamycin 42-ester with (tetrahydropyran-2-yloxy)acetic acid or a pharmaceutically acceptable salt thereof.

6. The compound of claim 1 which is rapamycin 42-ester with hydroxyacetic acid or a pharmaceutically acceptable salt thereof.

7. The compound of claim 1 which is rapamycin 42-ester with 2,2-dimethyl-3-(tetrahydropyran-2-yloxy)propionic acid or a pharmaceutically acceptable salt thereof.

8. The compound of claim 1 which is rapamycin 42-ester with 3-hydroxy-2,2-dimethylpropionic acid or a pharmaceutically acceptable salt thereof.

9. The compound of claim 1 which is rapamycin 42-ester with 2,2-dimethyl[1,3]dioxalane-4-carboxylic acid or a pharmaceutically acceptable salt thereof.

10. The compound of claim 1 which is rapamycin 31,42-diester with 2,2-dimethyl[1,3]dioxalane-4-carboxylic acid or a pharmaceutically acceptable salt thereof.

11. The compound of claim 1 which is rapamycin 42-ester with 2,3-dihydroxypropionic acid or a pharmaceutically acceptable salt thereof.

12. The compound of claim 1 which is rapamycin 42-ester with 2,2-dimethyl[1,3]dioxane-5-carboxylic acid or a pharmaceutically acceptable salt thereof.

13. The compound of claim 1 which is rapamycin 42-ester with 3-hydroxy-2-hydroxymethylpropionic acid or a pharmaceutically acceptable salt thereof.

14. The compound of claim 1 which is rapamycin 42-ester with 2,2,5-trimethyl[1,3]dioxane-5-carboxylic acid or a pharmaceutically acceptable salt thereof.

15. The compound of claim 1 which is rapamycin 42-ester with 2,2-bis(hydroxymethyl)propionic acid or a pharmaceutically acceptable salt thereof.

16. The compound of claim 1 which is rapamycin 42-ester with 2,2-dimethyl-5-(2-trimethylsilanylethoxymethyl)[1,3]-dioxane-5-carboxylic acid or a pharmaceutically acceptable salt thereof.

17. The compound of claim 1 which is rapamycin 42-ester with 3-methyl-1,5-dioxa-spiro[5.5]undecane 3-carboxylic acid or a pharmaceutically acceptable salt thereof.

18. The compound of claim 1 which is rapamycin 31,42-diester with 3-methyl-1,5-dioxa-spiro[5.5]undecane 3-carboxylic acid or a pharmaceutically acceptable salt thereof.

19. A method of treating transplantation rejection or graft vs. host disease in a mammal in need thereof, which comprises administering to said mammal an antirejection effective amount of a compound of the structure

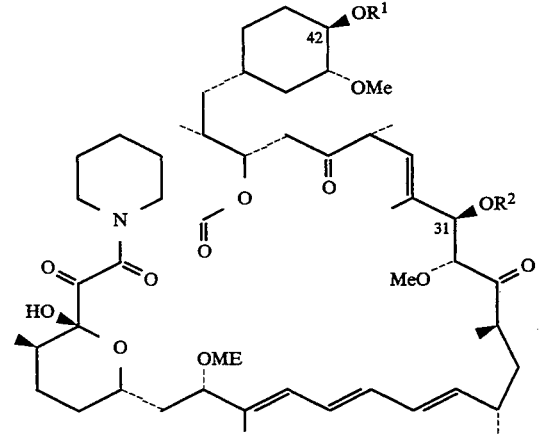

wherein $R^1$ and $R^2$ are each, independently, hydrogen or —$CO(CR^3R^4)_b(CR^5R^6)_dCR^7R^8R^9$;

$R^3$ and $R^4$ are each, independently, hydrogen, alkyl of 1-6 carbon atoms, alkenyl of 2-7 carbon atoms, alkynyl of 2-7 carbon atoms, trifluoromethyl, or —F;

$R^5$ and $R^6$ are each, independently, hydrogen, alkyl of 1-6 carbon atoms, alkenyl of 2-7 carbon atoms, alkynyl of 2-7 carbon atoms, —$(CR^3R^4)_fOR^{10}$, —$CF_3$, —F, or —$CO_2R^{11}$, or $R^5$ and $R^6$ may be taken together to form X or a cycloalkyl ring of 3-8 carbon atoms that is optionally mono-, di-, or tri-substituted with —(CR$^3$R$^4$)$_f$OR$^{10}$;

R$^7$ is hydrogen, alkyl of 1-6 carbon atoms, alkenyl of 2-7 carbon atoms, alkynyl of 2-7 carbon atoms, —(CR$^3$R$^4$)$_f$OR$^{10}$, —CF$_3$, —F, or —CO$_2$R$^{11}$;

R$^8$ and R$^9$ are each, independently, hydrogen, alkyl of 1-6 carbon atoms, alkenyl of 2-7 carbon atoms, alkynyl of 2-7 carbon atoms, —(CR$^3$R$^4$)$_f$OR$^{10}$, —CF$_3$, —F, or —CO$_2$R$^{11}$, or R$^8$ and R$^9$ may be taken together to form X or a cycloalkyl ring of 3-8 carbon atoms that is optionally mono-, di-, or tri-substituted with —(CR$^3$R$^4$)$_f$OR$^{10}$;

R$^{10}$ is hydrogen, alkyl of 1-6 carbon atoms, alkenyl of 2-7 carbon atoms, alkynyl of 2-7 carbon atoms, tri-(alkyl of 1-6 carbon atoms)silyl, tri-(alkyl of 1-6 carbon atoms)silylethyl, triphenylmethyl, benzyl, alkoxymethyl of 2-7 carbon atoms, tri-(alkyl of 1-6 carbon atoms)silylethoxymethyl, chloroethyl, or tetrahydropyranyl;

R$^{11}$ is hydrogen, alkyl of 1-6 carbon atoms, alkenyl of 2-7 carbon atoms, alkynyl of 2-7 carbon atoms, or phenylalkyl of 7-10 carbon atoms;

X is 5-(2,2-di-(alkyl of 1-6 carbon atoms))[1,3]dioxanyl, 5-(2,2-di-(cycloalkyl of 3-8 carbon atoms))[1,3]dioxanyl, 4-(2,2-di-(alkyl of 1-6 carbon atoms))[1,3]dioxanyl, 4-(2,2-di-(cycloalkyl of 3-8 carbon atoms))[1,3]dioxanyl, 4-(2,2-di-(alkyl of 1-6 carbon atoms))[1,3]dioxalanyl, or 4-(2,2-di-(cycloalkyl of 3-8 carbon atoms))[1,3]dioxalanyl;

b=0-6;
d=0-6; and
f=0-6 with the proviso that R$^1$ and R$^2$ are both not hydrogen and further provided that either R$^1$ or R$^2$ contains at least one —(CR$^3$R$^4$)$_f$OR$^{10}$, X, or —(CR$^3$R$^4$)$_f$OR$^{10}$ substituted cycloalkyl of 3-8 carbon atoms group, or a pharmaceutically acceptable salt thereof.

20. A method of treating a fungal infection in a mammal in need thereof, which comprises administering to said mammal an antifungal effective amount of a compound of the structure

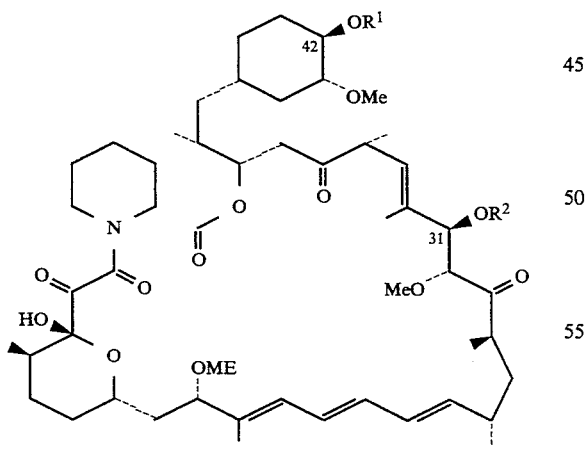

wherein R$^1$ and R$^2$ are each, independently, hydrogen or —CO(CR$^3$R$^4$)$_b$(CR$^5$R$^6$)$_d$CR$^7$R$^8$9$^9$;

R$^3$ and R$^4$ are each, independently, hydrogen, alkyl of 1-6 carbon atoms, alkenyl of 2-7 carbon atoms, alkynyl of 2-7 carbon atoms, trifluoromethyl, or —F;

R$^5$ and R$^6$ are each, independently, hydrogen, alkyl of 1-6 carbon atoms, alkenyl of 2-7 carbon atoms, alkynyl of 2-7 carbon atoms, —(CR$^3$R$^4$)$_f$OR$^{10}$,—CF$_3$, —F, or —CO$_2$R$^{11}$, or R$^5$ and R$^6$ may be taken together to form X or a cycloalkyl ring of 3-8 carbon atoms that is optionally mono-, di-, or tri-substituted with —(CR$^3$R$^4$)$_f$OR$^{10}$;

R$^7$ is hydrogen, alkyl of 1-6 carbon atoms, alkenyl of 2-7 carbon atoms, alkynyl of 2-7 carbon atoms, —(CR$^3$R$^4$)$_f$OR$^{10}$, —CF$_3$, —F, or —CO$_2$R$_{11}$;

R$^8$ and R$^9$ are each, independently, hydrogen, alkyl of 1-6 carbon atoms, alkenyl of 2-7 carbon atoms, alkynyl of 2-7 carbon atoms, —(CR$^3$R$^4$)$_f$OR$^{10}$, —CF$_3$, —F, or —CO$_2$R$^{11}$, or R$^8$ and R$^9$ may be taken together to form X or a cycloalkyl ring of 3-8 carbon atoms that is optionally mono-, di-, or tri-substituted with —(CR$^3$R$^4$)$_f$OR$^{10}$;

R$^{10}$ is hydrogen, alkyl of 1-6 carbon atoms, alkenyl of 2-7 carbon atoms, alkynyl of 2-7 carbon atoms, tri-(alkyl of 1-6 carbon atoms)silyl, tri-(alkyl of 1-6 carbon atoms)silylethyl, triphenylmethyl, benzyl, alkoxymethyl of 2-7 carbon atoms, tri-(alkyl of 1-6 carbon atoms)silylethoxymethyl, chloroethyl, or tetrahydropyranyl;

R$^{11}$ is hydrogen, alkyl of 1-6 carbon atoms, alkenyl of 2-7 carbon atoms, alkynyl of 2-7 carbon atoms, or phenylalkyl of 7-10 carbon atoms;

X is 5-(2,2-di-(alkyl of 1-6 carbon atoms))[1,3]dioxanyl, 5-(2,2-di-(cycloalkyl of 3-8 carbon atoms))[1,3]dioxanyl, 4-(2,2-di-(alkyl of 1-6 carbon atoms))[1,3]dioxanyl, 4-(2,2-di-(cycloalkyl of 3-8 carbon atoms))[1,3]dioxanyl, 4-(2,2-di-(alkyl of 1-6 carbon atoms))[1,3]dioxalanyl, or 4-(2,2-di-(cycloalkyl of 3-8 carbon atoms))[1,3]dioxalanyl;

b=0-6;
d=0-6; and
f=0-6 with the proviso that R$^1$ and R$^2$ are both not hydrogen and further provided that either R$^1$ or R$^2$ contains at least one —(CR$^3$R$^4$)$_f$OR$^{10}$, X, or —(CR$^3$R$^4$)$_f$OR$^{10}$ substituted cycloalkyl of 3-8 carbon atoms group, or a pharmaceutically acceptable salt thereof.

21. A method of treating rheumatoid arthritis in a mammal in need thereof, which comprises administering to said mammal an antiarthritis effective amount of a compound of the structure

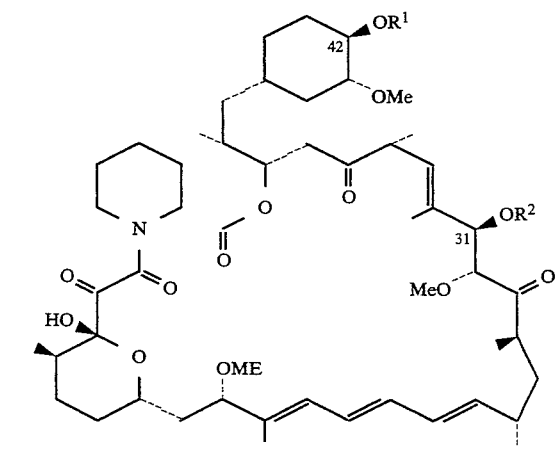

wherein R$^1$ and R$^2$ are each, independently, hydrogen or —CO(CR$^3$R$^4$)$_b$(CR$^5$R$^6$)$_d$CR$^7$R$^8$R$^9$;

R$^3$ and R$^4$ are each, independently, hydrogen, alkyl of 1-6 carbon atoms, alkenyl of 2-7 carbon atoms, alkynyl of 2-7 carbon atoms, trifluoromethyl, or —F;

$R^5$ and $R^6$ are each, independently, hydrogen, alkyl of 1-6 carbon atoms, alkenyl of 2-7 carbon atoms, alkynyl of 2-7 carbon atoms, —$(CR^3R^4)_fOR^{10}$, —$CF_3$, —F, or —$CO_2R^{11}$, or $R^5$ and $R^6$ may be taken together to form X or a cycloalkyl ring of 3-8 carbon atoms that is optionally mono-, di-, or tri-substituted with —$(CR^3R^4)_fOR^{10}$;

$R^7$ is hydrogen, alkyl of 1-6 carbon atoms, alkenyl of 2-7 carbon atoms, alkynyl of 2-7 carbon atoms, —$(CR^3R^4)_fOR^{10}$, —$CF_3$, —F, or —$CO_2R^{11}$;

$R^8$ and $R^9$ are each, independently, hydrogen, alkyl of 1-6 carbon atoms, alkenyl of 2-7 carbon atoms, alkynyl of 2-7 carbon atoms, —$(CR^3R^4)_fOR^{10}$, —$CF_3$, —F, or —$CO_2R^{11}$, or $R^8$ and $R^9$ may be taken together to form X or a cycloalkyl ring of 3-8 carbon atoms that is optionally mono-, di-, or tri-substituted with —$(CR^3R^4)_fOR^{10}$;

$R^{10}$ is hydrogen, alkyl of 1-6 carbon atoms, alkenyl of 2-7 carbon atoms, alkynyl of 2-7 carbon atoms, tri-(alkyl of 1-6 carbon atoms)silyl, tri-(alkyl of 1-6 carbon atoms)silylethyl, triphenylmethyl, benzyl, alkoxymethyl of 2-7 carbon atoms, tri-(alkyl of 1-6 carbon atoms)silylethoxymethyl, chloroethyl, or tetrahydropyranyl;

$R^{11}$ is hydrogen, alkyl of 1-6 carbon atoms, alkenyl of 2-7 carbon atoms, alkynyl of 2-7 carbon atoms, or phenylalkyl of 7-10 carbon atoms;

X is 5-(2,2di-(alkyl of 1-6 carbon atoms))[1,3]dioxanyl, 5-(2,2-di-(cycloalkyl of 3-8 carbon atoms))[1,3]dioxanyl, 4-(2,2-di-(alkyl of 1-6 carbon atoms))[1,3]dioxanyl, 4-(2,2-di-(cycloalkyl of 3-8 carbon atoms))[1,3]dioxanyl, 4-(2,2-di-(alkyl of 1-6 carbon atoms))[3]dioxalanyl, or 4-(2,2-di-(cycloalkyl of 3-8 carbon atoms))[1,3]dioxalanyl;

b=0-6;
d=0-6; and
f=0-6 with the proviso that $R^1$ and $R^2$ are both not hydrogen and further provided that either $R^1$ or $R^2$ contains at least one —$(CR^3R^4)_fOR^{10}$, X, or —$(CR^3R^4)_fOR^{10}$ substituted cycloalkyl of 3-8 carbon atoms group, or a pharmaceutically acceptable salt thereof.

22. A method of treating restenosis in a mammal in need thereof, which comprises administering to said mammal an antiproliferative effective amount of a compound of the structure

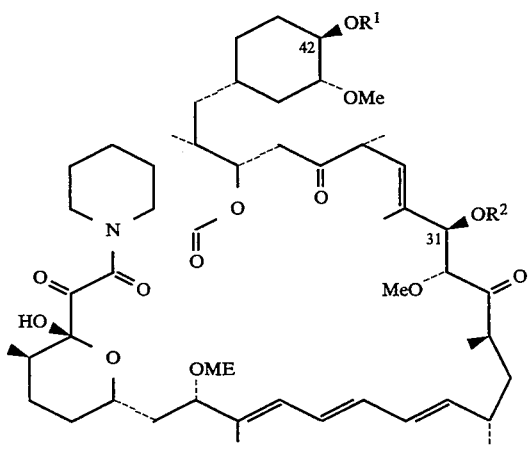

wherein $R^1$ and $R^2$ are each, independently, hydrogen or —$CO(CR^3R^4)_bCR^5R^6)_dCR^7R^8R^9$;

$R^3$ and $R^4$ are each, independently, hydrogen, alkyl of 1-6 carbon atoms, alkenyl of 2-7 carbon atoms, alkynyl of 2-7 carbon atoms, trifluoromethyl, or —F;

$R^5$ and $R^6$ are each, independently, hydrogen, alkyl of 1-6 carbon atoms, alkenyl of 2-7 carbon atoms, alkynyl of 2-7 carbon atoms, —$(CR^3R^4)_fOR^{10}$, —$CF_3$, —F, or —$CO_2R^{11}$, or $R^5$ and $R^6$ may be taken together to form X or a cycloalkyl ring of 3-8 carbon atoms that is optionally mono-, di-, or tri-substituted with —$(CR^3R^4)_fOR^{10}$;

$R^7$ is hydrogen, alkyl of 1-6 carbon atoms, alkenyl of 2-7 carbon atoms, alkynyl of 2-7 carbon atoms, —$(CR^3R^4)_fOR^{10}$, —$CF_3$, —F, or —$CO_2R^{11}$;

$R^8$ and $R^9$ are each, independently, hydrogen, alkyl of 1-6 carbon atoms, alkenyl of 2-7 carbon atoms, alkynyl of 2-7 carbon atoms, —$(CR^3R^4)_fOR^{10}$, —$CF_3$, —F, or —$CO_2R^{11}$, or $R^8$ and $R^9$ may be taken together to form X or a cycloalkyl ring of 3-8 carbon atoms that is optionally mono-, di-, or tri-substituted with —$(CR^3R^4)_fOR^{10}$;

$R^{10}$ is hydrogen, alkyl of 1-6 carbon atoms, alkenyl of 2-7 carbon atoms, alkynyl of 2-7 carbon atoms, tri-(alkyl of 1-6 carbon atoms)silyl, tri-(alkyl of 1-6 carbon atoms)silylethyl, triphenylmethyl, benzyl, alkoxymethyl of 2-7 carbon atoms, tri-(alkyl of 1-6 carbon atoms)silylethoxymethyl, chloroethyl, or tetrahydropyranyl;

$R^{11}$ is hydrogen, alkyl of 1-6 carbon atoms, alkenyl of 2-7 carbon atoms, alkynyl of 2-7 carbon atoms, or phenylalkyl of 7-10 carbon atoms;

X is 5-(2,2-di-(alkyl of 1-6 carbon atoms))[1,3]dioxanyl, 5-(2,2-di-(cycloalkyl of 3-8 carbon atoms))[1,3]dioxanyl, 4-(2,2-di-(alkyl of 1-6 carbon atoms))[1,3]dioxanyl, 4-(2,2-di-(cycloalkyl of 3-8 carbon atoms))[1,3]dioxanyl, 4-(2,2-di-(alkyl of 1-6 carbon atoms))[1,3]dioxalanyl, or 4-(2,2-di-(cycloalkyl of 3-8 carbon atoms))[1,3]dioxalanyl;

b=0-6;
d=0-6; and
f=0-6 with the proviso that $R^1$ and $R^2$ are both not hydrogen and further provided that either $R^1$ or $R^2$ contains at least one —$(CR^3R^4)_fOR^{10}$, X, or —$(CR^3R^4)_fOR^{10}$ substituted cycloalkyl of 3-8 carbon atoms group, or a pharmaceutically acceptable salt thereof.

23. A method of treating pulmonary inflammation in a mammal in need thereof, which comprises administering to said mammal an antiinflammatory effective amount of a compound of the structure

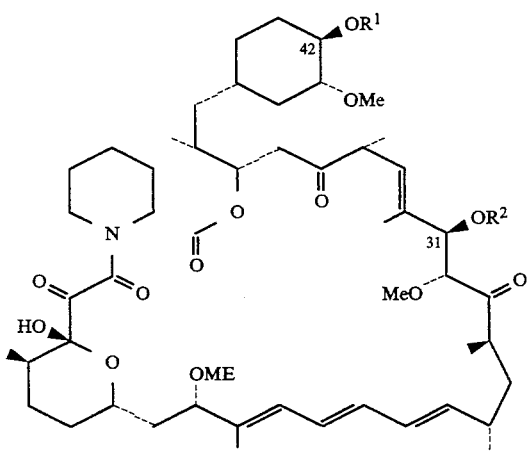

wherein $R^1$ and $R^2$ are each, independently, hydrogen or $-CO(CR^3R^4)_b(CR^5R^6)_dCR^7R^8R^9$;

$R^3$ and $R^4$ are each, independently, hydrogen, alkyl of 1–6 carbon atoms, alkenyl of 2–7 carbon atoms, alkynyl of 2–7 carbon atoms, trifluoromethyl, or —F;

$R^5$ and $R^6$ are each, independently, hydrogen, alkyl of 1–6 carbon atoms, alkenyl of 2–7 carbon atoms, alkynyl of 2–7 carbon atoms, $-(CR^3R^4)_fOR^{10}$, $-CF_3$, —F, or $-CO_2R^{11}$, or $R^5$ and $R^6$ may be taken together to form X or a cycloalkyl ring of 3–8 carbon atoms that is optionally mono-, di-, or tri-substituted with $-(CR^3R^4)_fOR^{10}$;

$R^7$ is hydrogen, alkyl of 1–6 carbon atoms, alkenyl of 2–7 carbon atoms, alkynyl of 2–7 carbon atoms, $-(CR^3R^4)_fOR^{10}$, $-CF_3$, —F, or $-CO_2R^{11}$;

$R^8$ and $R^9$ are each, independently, hydrogen, alkyl of 1–6 carbon atoms, alkenyl of 2–7 carbon atoms, alkynyl of 2–7 carbon atoms, $-(CR^3R^4)_fOR^{10}$, $-CF_3$, —F, or $-CO_2R^{11}$, or $R^8$ and $R^9$ may be taken together to form X or a cycloalkyl ring of 3–8 carbon atoms that is optionally mono-, di-, or tri-substituted with $-(CR^3R^4)_fOR^{10}$;

$R^{10}$ is hydrogen, alkyl of 1–6 carbon atoms, alkenyl of 2–7 carbon atoms, alkynyl of 2–7 carbon atoms, tri-(alkyl of 1–6 carbon atoms)silyl, tri-(alkyl of 1–6 carbon atoms)silylethyl, triphenylmethyl, benzyl, alkoxymethyl of 2–7 carbon atoms, tri-(alkyl of 1–6 carbon atoms)silylethoxymethyl, chloroethyl, or tetrahydropyranyl;

$R^{11}$ is hydrogen, alkyl of 1–6 carbon atoms, alkenyl of 2–7 carbon atoms, alkynyl of 2–7 carbon atoms, or phenylalkyl of 7–10 carbon atoms;

X is 5-(2,2-di-(alkyl of 1–6 carbon atoms))[1,3]dioxanyl, 5-(2,2-di-(cycloalkyl of 3–8 carbon atoms))[1,3]dioxanyl, 4-(2,2-di-(alkyl of 1–6 carbon atoms))[1,3]dioxanyl, 4-(2,2-di-(cycloalkyl of 3–8 carbon atoms))[1,3]dioxanyl, 4-(2,2-di-(alkyl of 1–6 carbon atoms))[1,3]dioxalanyl, or 4-(2,2-di-(cycloalkyl of 3–8 carbon atoms))[1,3]dioxalanyl;

b=0–6;
d=0–6; and
f=0–6 with the proviso that $R^1$ and $R^2$ are both not hydrogen and further provided that either $R^1$ or $R^2$ contains at least one $-(CR^3R^4)_fOR^{10}$, X, or $-(CR^3R^4)_fOR^{10}$ substituted cycloalkyl of 3–8 carbon atoms group, or a pharmaceutically acceptable salt thereof.

24. A pharmaceutical composition which comprises a compound of the structure

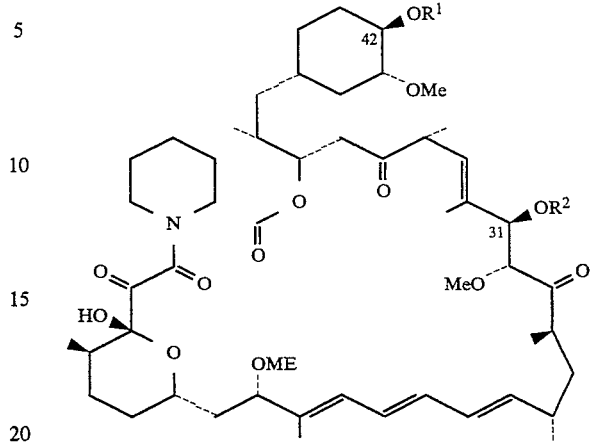

wherein $R^1$ and $R^2$ are each, independently, hydrogen or $-CO(CR^3R^4)_bCR^5R^6)_dCR^7R^8R^9$; $R^3$ and $R^4$ are each, independently, hydrogen, alkyl of 1–6 carbon atoms, alkenyl of 2–7 carbon atoms, alkynyl of 2–7 carbon atoms, trifluoromethyl, or —F;

$R^5$ and $R^6$ are each, independently, hydrogen, alkyl of 1–6 carbon atoms, alkenyl of 2–7 carbon atoms, alkynyl of 2–7 carbon atoms, $-(CR^3R^4)_fOR^{10}$, $-CF_3$, —F, or $-CO_2R^{11}$, or $R^5$ and $R^6$ may be taken together to form X or a cycloalkyl ring of 3–8 carbon atoms that is optionally mono-, di-, or tri-substituted with $-(CR^3R^4)_fOR^{10}$;

$R^7$ is hydrogen, alkyl of 1–6 carbon atoms, alkenyl of 2–7 carbon atoms, alkynyl of 2–7 carbon atoms, $-(CR^3R^4)_fOR^{10}$, $-CF_3$, —F, or $-CO_2R^{11}$;

$R^8$ and $R^9$ are each, independently, hydrogen, alkyl of 1–6 carbon atoms, alkenyl of 2–7 carbon atoms, alkynyl of 2–7 carbon atoms, $-(CR^3R^4)_fOR^{10}$, $-CF_3$—F, or $-CO_2R^{11}$, or $R^8$ and $R^9$ may be taken together to form X or a cycloalkyl ring of 3–8 carbon atoms that is optionally mono-, di-, or tri-substituted with $-(CR^3R^4)_fOR^{10}$;

$R^{10}$ is hydrogen, alkyl of 1–6 carbon atoms, alkenyl of 2–7 carbon atoms, alkynyl of 2–7 carbon atoms, tri-(alkyl of 1–6 carbon atoms)silyl, tri-(alkyl of 1–6 carbon atoms)silylethyl, triphenylmethyl, benzyl, alkoxymethyl of 2–7 carbon atoms, tri-(alkyl of 1–6 carbon atoms)silylethoxymethyl, chloroethyl, or tetrahydropyranyl;

$R^{11}$ is hydrogen, alkyl of 1–6 carbon atoms, alkenyl of 2–7 carbon atoms, alkynyl of 2–7 carbon atoms, or phenylalkyl of 7–10 carbon atoms;

X is 5-(2,2-di-(alkyl of 1–6 carbon atoms))[1,3]dioxanyl, 5-(2,2-di-(cycloalkyl of 3–8 carbon atoms))[1,3]dioxanyl, 4-(2,2-di-(alkyl of 1–6 carbon atoms))[1,3]dioxanyl, 4-(2,2-di-(cycloalkyl of 3–8 carbon atoms))[1,3]dioxanyl, 4-(2,2-di-(alkyl of 1–6 carbon atoms))[1,3]dioxalanyl, or 4-(2,2-di-(cycloalkyl of 3–8 carbon atoms))[1,3]dioxalanyl;

b=0–6;
d=0–6; and
f=0–6 with the proviso that $R^1$ and $R^2$ are both not hydrogen and further provided that either $R^1$ or $R^2$ contains at least one $-(CR^3R^4)_fOR^{10}$, X, or $-(CR^3R^4)_fOR^{10}$ substituted cycloalkyl of 3–8 carbon atoms group, or a pharmaceutically acceptable salt thereof, and a pharmaceutical carrier.

* * * * *

UNITED STATES PATENT AND TRADEMARK OFFICE
CERTIFICATE OF CORRECTION

PATENT NO.    : 5,362,718

DATED         : November 8, 1994

INVENTORS     : Jerauld S. Skotnicki, Christina L. Leone, Guy A. Schiehser

It is certified that errors appear in the above-identified patent and that said Letters Patent is hereby corrected as shown below:

On Page 2 of the Abstract, first column, and in the Patent column 2, lines 1-19; column 14, lines 45-64; column 16, lines 38-57; column 17, lines 41-60; column 18, lines 45-64; column 19, lines 48-67; column 21, lines 1-19; and column 22, lines 3-22, please delete the structure and insert therefor:

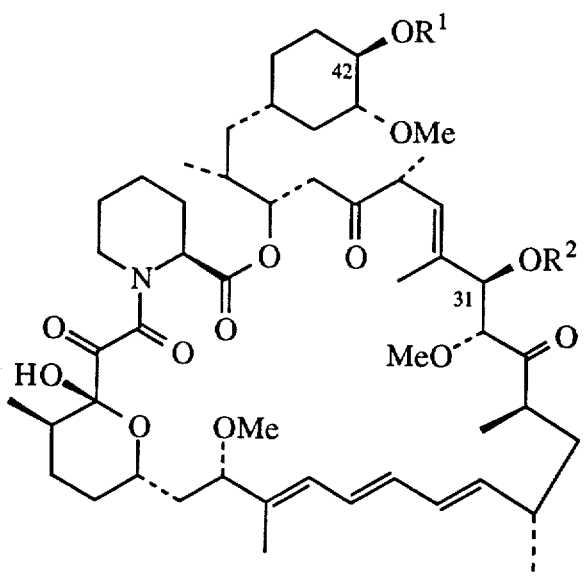

Signed and Sealed this

Twelfth Day of August, 1997

Attest:

BRUCE LEHMAN

Attesting Officer

Commissioner of Patents and Trademarks